United States Patent [19]
DeHaven-Hudkins et al.

[11] Patent Number: 5,430,036
[45] Date of Patent: Jul. 4, 1995

[54] 6,11-SUBSTITUTED-6,11-DIHYDROBEN-ZO[B]QUINOLIZINIUM SALTS AND COMPOSITIONS AND METHOD OF USE THEREOF

[75] Inventors: Diane L. DeHaven-Hudkins, W. Pikeland Township, Chester County; Providence Township, Montgomery County; John P. Mallamo, Uwchlan Township, Chester County; Matthew Township, Bucks County, all of Pa.

[73] Assignee: Sterling Winthrop Inc., Malvern, Pa.

[21] Appl. No.: 328,941

[22] Filed: Oct. 25, 1994

Related U.S. Application Data

[63] Continuation of Ser. No. 121,626, Sep. 14, 1993, abandoned.

[51] Int. Cl.[6] .................. A61K 31/435; C07D 471/00
[52] U.S. Cl. ........................................ 514/281; 546/43
[58] Field of Search ............................ 546/43; 514/281

[56] References Cited

U.S. PATENT DOCUMENTS 3,517,073  6/1970  Fields ................................. 568/735

OTHER PUBLICATIONS

Fields, et al., J. Org. Chem. 1968, 33(1), 390–395.
Fields and Regan, J. Org. Chem. 1971, 36(20), 2986–2990.
Fields and Regan, J. Org. Chem. 1971, 36(20), 2991–2994.
Fields, J. Org. Chem. 1971, 36(20), 3002–3005.
Westerman and Bradsher, J. Org. Chem. 1971, 36(7), 969–970.
Bradsher and Day, J. Het. Chem. 1973, 10, 1031–1033.
Fields and Regan, J. Org. Chem. 1970, 35(6), 1870–1875.
Fields et al., J. Org. Chem. 1971, 36(20), 2995–3001.
Fields and Miller, J. Het Chem. 1970, 7, 91–97.
Bradsher and Stone, J. Org. Chem. 1968, 33(2), 519–523.
Bradsher and Solomons, J. Am. Chem. Soc. 1958, 80, 933–934.
Bradsher and Stone, J. Org. Chem. 1969, 34(6), 1700–1702.
Burnham and Bradsher, J. Org. Chem. 1972, 37(3), 355–358.
Parham et al., J. Org. Chem. 1972, 37(3), 358–362.
Bradsher et al., J. Am. chem. Soc. 1977, 99(8), 2588–2591.
Bradsher et al., J. Org. Chem. 1978, 43(5), 822–827.
Westerman and Bradsher, J. Org. Chem. 1978, 43(15), 3002–3006.
Westerman and Bradsher, J. Org. Chem. 1979, 44(5), 727–733.
Bradsher et al., J. Org. Chem. 1979, 44(8), 1199–1201.
Hart et al., Tetrahedron Letters 1975, 52, 4639–4642.

*Primary Examiner*—Mukund J. Shah
*Assistant Examiner*—Matthew V. Grumbling
*Attorney, Agent, or Firm*—Michael D. Alexander; Paul E. Dupont

[57] ABSTRACT

6,11-Substituted-6,11-dihydrobenzo[b]quinolizinium salts, pharmaceutical compositions containing them and methods for the treatment or prevention of neurodegenerative disorders or neurotoxic injuries utilizing them.

23 Claims, No Drawings

6,11-SUBSTITUTED-6,11-DIHYDROBENZO[B-]QUINOLIZINIUM SALTS AND COMPOSITIONS AND METHOD OF USE THEREOF

CROSS REFERENCE TO RELATED APPLICATIONS

This application is a continuation of our application Ser. No. 08/121,626, filed Sep. 14, 1993, now abandoned.

BACKGROUND OF THE INVENTION (a) Field of the Invention

The invention relates to 6,11-substituted-6,11-dihydrobenzo[b]quinolizinium salts, to compositions containing the same and to the method of use thereof in the treatment or prevention of neurodegenerative disorders or neurotoxic injuries.

(b) Information Disclosure Statement

Fields, U.S. Pat. No. 3,517,073 issued Jun. 23, 1970, discloses compounds of the formula:

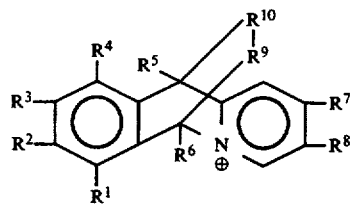

wherein each of $R^1$, $R^2$, $R^3$ and $R^4$ when taken separately, is hydrogen, lower alkyl, lower aryl, lower acyloxy, lower alkoxy, nitro, halogen, lower acylamino, di(lower alkyl) amino; one group of $R^1$ and $R^2$, $R^2$ and $R^3$, and $R^3$ and $R^4$, preferably $R^1$ and $R^2$, and $R^3$ and $R^4$, each group when taken together, represents a fused ring system containing up to three 6-member carbocyclic and nitrogen-containing heterocyclic rings at least one of which is an aromatic ring, and having no more than two nuclear nitrogens in any ring, which may be unsubstituted or substituted with one or more of the substituents defined by $R^1$, $R^2$, $R^3$ and $R^4$; each of $R^5$ and $R^6$, when taken separately is hydrogen, lower alkyl or lower aryl; each of $R^7$ and $R^8$, when taken separately, is hydrogen; $R^7$ and $R^8$, when taken together, represent a fused ring system as defined hereinbefore; $R^9$, when taken individually, is methylene or lower alkyl, lower aryl, lower alkenyl, halogen, or cyano substituted methylene; $R^{10}$, when taken individually, is a protected carbonyl group; $R^9$ and $R^{10}$, when taken together, represent a fused aromatic carbocyclic or heterocyclic ring system, whose valence bonds are from adjacent carbons, containing up to three 6-membered carbocyclic and nitrogen-containing heterocyclic rings having no more than two nitrogens in any ring and which may be substituted with one or more of the substituents defined by $R^1$, $R^2$, $R^3$ and $R^4$. Among the compounds specifically disclosed are 12,12-diethoxy-11-methyl-9,10-ethano-9,10-dihydro-4a-azoniaanthracene perchlorate and 9,10-(O-benzeno)-9,10-dihydro-5-methyl-4a-azoniaanthracene perchlorate. Also disclosed are compounds of the formula:

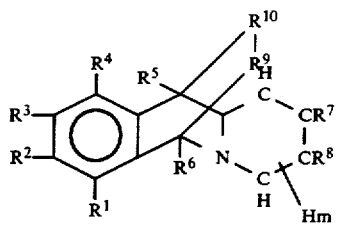

wherein $R^1$-$R^{10}$ are as defined above and m is an odd integer having a value of from 1 to 5, inclusive. Among the compounds specifically disclosed are 12,12-diethoxy-11-methyl-9,10-ethano-4a-aza-1,2,3,4,4a,9,9a,10-octahydroanthracene perchlorate acid salt, 9,10-(O-benzeno)-5-methyl-4a-aza-1,2,3,4,4a,9,9a,10-octahydroanthracene and 12,12-diethoxy-9,10-ethano-11-bromo-4a-aza-1,2,3,-4,4a,9,9a,10-octahydroanthracene. The above-described compounds are disclosed as being intermediates in the synthesis of 2-napthol derivatives and various anthracene derivatives.

Fields et al., J. Org. Chem. 1968, 33(1), 390-395, disclose a series of sixteen Diels-Alder adducts prepared from a 4a-azoniaanthracene ion and various dienophiles. Among the compounds specifically disclosed are 12-ethyl,12-hydroxymethyl and 12-ethylene-9,10-dihydro-4a-azonia-9,10-ethanoanthracene bromides; 12-phenyl-12-(4-morpholinyl), 12-methyl-12-(1-methylethylene), 12,12-diethoxy-11-bromo and 12-diethylamino-11-phenyl-9,10-dihydro-4a-azonia-9,10-ethanoanthracene perchlorates, as well as 9,10[1',2']cyclopentyl and 9,10[2',3']tetrahydropyranyl-9,10-dihydro-4a-azoniaanthracene perchlorates. No utility is disclosed for these compounds.

Fields and Regan, J. Org. Chem. 1971, 36(20), 2986-2990, disclose compounds of the formula:

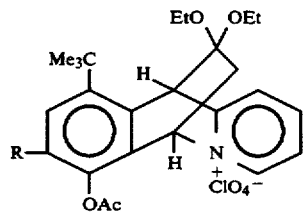

wherein R is H, Br, or OAc, as intermediates in the synthesis of substituted 8-tert-butyl-1-(2-pyridyl)napthalenes.

Fields and Regan, J. Org. Chem. 1971, 36(20), 2991-2994, disclose compounds of the formula:

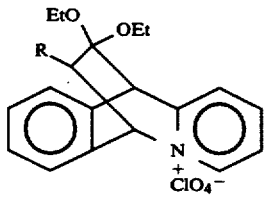

wherein R is H, $CH_3$, $C_6H_5$, or Br, as intermediates in the synthesis of 2-pyridylnapthols.

Fields, J. Org. Chem. 1971, 36(20), 3002-3005, discloses a series of substituted 12,12-diethoxy-9,10-ethano-9,10-dihydro-4a-azoniaanthracenes and the corresponding derivatives wherein the pyridinium moiety is partially or completely reduced, as intermediates in the synthesis of substituted 2-napthols. Among the compounds specifically disclosed is 12,12-diethoxy-5,11-dimethyl-9,10-ethano-9,10-dihydro-4a-azoniaanthracene perchlorate. Also disclosed is a series of substituted 9,10-(O-benzeno)-9,10-dihydro-4a-azoniaanthracenes and the corresponding derivatives wherein the pyridinium moiety is partially or completely reduced, as intermediates in the synthesis of substituted anthracenes. Among the compounds specifically disclosed is 9,10-(O-benzeno)-9,10-dihydro-4a-azoniaanthracene perchlorate.

Westerman and Bradsher, J. Org. Chem. 1971, 36(7), 969-970, disclose compounds of the formula:

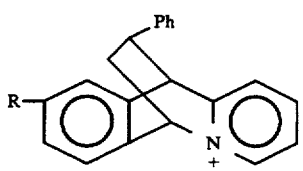

wherein R is $CH_3$, $CH(CH_3)_2$, H, F, I, Cl, Br, $CO_2H$, $CO_2CH_3$, or $NO_2$. No utility is disclosed for these compounds.

Bradsher and Day, J. Het. Chem. 1973, 10, 1031-1033, disclose four Diels-Alder adducts prepared from acridizinium perchlorate and cyclopentadiene, methyl vinyl ether, norbornadiene and maleic anhydride. No utility is disclosed for these compounds.

Fields and Regan, J. Org. Chem. 1970, 35(6), 1870-1875, disclose compounds of the formula:

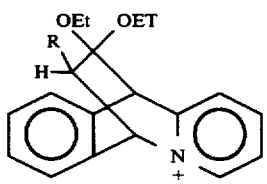

wherein R is H, $CH_3$ or $C_6H_5$. Also specifically disclosed are 9,10-dihydro-12,12-dimethoxy-11,11-dimethyl-4a-azonia-9,10-ethanoanthracene perchlorate and 9,10-dihydro-9,11-dimethyl-12,12-diethoxy-4a-azonia-9,10-ethanoanthracene perchlorate. The compounds are said to be intermediates in the synthesis of 9,10-dihydro-12-oxo-4a-azonia-9,10-ethanoanthracenes.

Fields et al., J. Org. Chem. 1971, 36(20), 2995-3001, disclose 9,10-dihydro-4a-azonia-9,10-O-benzenoanthracene perchlorate and several analogs as intermediates in the synthesis of various 9-(2-pyridyl)anthracenes.

Fields and Miller, J. Het. Chem. 1970, 7, 91-97, disclose a compound of the formula:

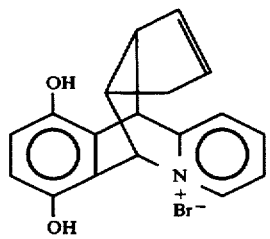

as an intermediate in the synthesis of the corresponding 5,8-dione salt.

Bradsher and Stone, J. Org. Chem. 1968, 33(2), 519-523, disclose a series of Diels-Alder adducts prepared from an acridizinium ion and maleic anhydride, maleate esters, fumarate esters and various para-substituted styrenes in which the para substituent is H, $CH_3$, $OCH_3$ or $NO_2$. No utility is disclosed for these compounds. A substantially similar disclosure for the preparation of Diels-Alder adducts from acridizinium bromide and maleic anhydride, maleate or fumarate esters can be found in Bradsher and Solomons, J. Am. Chem. Soc. 1958, 80, 933-934.

Bradsher and Stone, J. Org. Chem. 1969, 34(6), 1700-1702, disclose compounds of the formula:

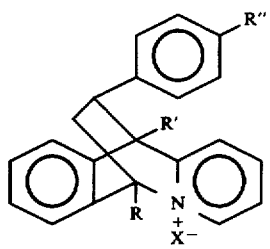

wherein R is H, or $CH_3$; R' is H, or $CH_3$; R" is $OCH_3$, $CH_3$, H, or $NO_2$; and $X^-$ is perchlorate; without an indication of utility. Also disclosed are the Diels-Alder adducts obtained from acridizinium perchlorate and diethyl maleate, diethyl fumarate or dimethyl maleate, without an indication of utility.

Burnham and Bradsher, J. Org. Chem. 1972, 37(3), 355-358, disclose compounds of the formula:

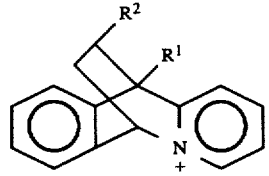

wherein $R^1$ is Ph, and $R^2$ is OEt; or $R^1$ is H, and $R^2$ is OEt, OBu, OAc, N-carbazolyl or 1-pyrrolidin-2-one, without an indication of utility Parham et al., J. Org. Chem. 1972, 37(3), 358-362, disclose compounds of the formula:

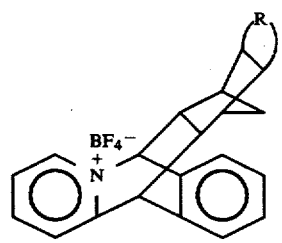

wherein R is $H_2$, $(CH_2)_3$, C(O)NHC(O), C(O)N($CH_3$)C(O), C(O)OC(O), $CH_2OCH_2$, or $CH_2NH_2^+CH_2$, without an indication of utility.

Bradsher et al., J. Am. Chem. Soc. 1977, 99(8), 2588-2591, disclose compounds of the formula:

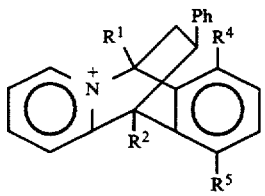

wherein: R¹=R²=R⁴=R⁵=H; R¹=Me, and R²=R⁴=R⁵=H; R¹=R⁴=R⁵=H, and R²=Me; and R¹=H, and R²=R⁴=R⁵=Me. No utility is disclosed for these compounds.

Bradsher et al., J. Org. Chem. 1978, 43(5), 822–827, disclose compounds of the formula:

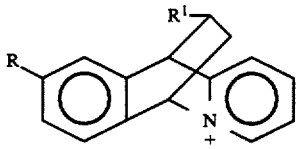

wherein: R¹ is OEt and R is Me, H, F, Cl, CO₂Me or NO₂; R¹ is O—Ph—p—X, wherein X is CH₃, OCH₃, H, C(O)CH₃, or NO₂, and R is hydrogen; and R¹ is N-carbazolyl and R is hydrogen. No utility is disclosed for these compounds.

Westerman and Bradsher, J. Org. Chem. 1978, 43(15), 3002–3006, disclose a series of Diels-Alder adducts prepared from an acridizinium ion and various unsymmetrical alkenes, without an indication of utility. Among the compounds specifically disclosed are 6,11[2′,3′]indanyl-6,11-dihydroacridizinium tetrafluoroborate, and 12-phenyl-13-(2-pyridyl)-6,11-dihydro-6,11-ethanoacridizinium tetrafluoroborate.

Westerman and Bradsher, J. Org. Chem. 1979, 44(5), 727–733, disclose a series of Diels-Alder adducts prepared from a substituted or unsubstituted acridizinium cation and various polarizable alkenes without an indication of utility. Among the compounds specifically disclosed are 12,12-diphenyl-6,11-dihydro-6,11-ethanoacridizinium perchlorate or bromide, 9-methyl-6,11[2′,3′]indanyl-6,11-dihydroacridizinium tetrafluoroborate, and 7,10-dimethyl-12-phenyl-12-(4-morpholinyl), 9-methyl-12-phenyl-12-(4-morpholinyl), 12-(2-pyridyl), and 9-methyl-12-(2-pyridyl)-6,11-dihydro-6,11-ethanoacridizinium tetrafluoroborates.

Bradsher et al., J. Org. Chem. 1979, 44(8), 1199–1201, disclose a series of Diels-Alder adducts prepared from a substituted or unsubstituted acridizinium ion and cyclopropene or 1-methylcyclopropene, without an indication of utility.

Hart et al., Tetrahedron Letters 1975, 52, 4639–4642, disclose a compound of the formula:

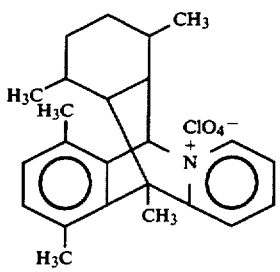

as an intermediate in the synthesis of 1,4,5,8,9-pentamethylanthracene.

SUMMARY OF THE INVENTION

The invention relates to compounds of the Formula I:

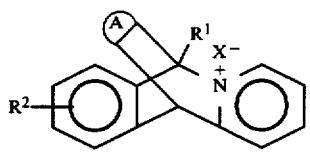

wherein:

R¹ is hydrogen, or lower-alkyl;

R² is hydrogen, or from one to four, the same or different, halogen substituents in any of the 7-,8-,9- or 10-positions;

A is cycloalkenyl, or said ring substituted at any available carbon atom thereof by lower-alkylidene; and X⁻ is an anion; or a hydrate thereof; or a stereoisomer thereof; with the proviso that when R¹ and R² are hydrogen and X⁻ is Br⁻, or ClO₄⁻, A cannot be [3′,4′]cyclopentenyl.

The compounds of Formula I bind to the PCP receptor and are thus useful in the treatment or prevention of neurodegenerative disorders or neurotoxic injuries.

Preferred compounds of Formula I above are those wherein:

R¹ is hydrogen, or methyl;

R² is hydrogen or a bromide or fluorine substituent in any of the 7-,8-,9- or 10-positions;

A is cyclopentenyl, or cyclohexenyl ring, or said cyclopentenyl ring substituted on any available carbon atom thereof by lower-alkylidene; and X⁻ is an anion;

Particularly preferred compounds of Formula I above are those wherein:

R¹ is hydrogen, or methyl;

R² is hydrogen or 9-Br or 9-F;

A is a [3′,4′]cyclohexenyl, [3′,4′]cyclopentenyl, or [5′-isopropylidene-[3′,4′]cyclopentenyl] ring; and X⁻ is an anion.

The invention further relates to pharmaceutical compositions which comprise a compound of Formula I:

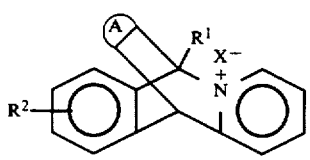

wherein:

R¹ is hydrogen, or lower-alkyl;

R² is hydrogen, or from one to four, the same or different, substituents in any of the 7-,8-,9- or 10- positions selected from the group consisting of halogen, nitro, lower-alkoxy, hydroxy, and lower-alkyl;

A is a member selected from the group consisting of cycloalkenyl, tetrahydrofuranyl, cycloalkyl, cycloalkenyl substituted at any available carbon atom thereof by lower-alkylidene; and phenyl; and X⁻ is an anion;

or a hydrate thereof; or a stereoisomer thereof; together with a pharmaceutically acceptable carrier, adjuvant, diluent, or vehicle; with the following provisos a) when R¹ is hydrogen, R² is 9-nitro and X⁻ is $ClO_4^-$, A cannot be [3',4']cyclopentenyl; b) when R¹ is hydrogen, R² is 7,10-dihydroxy and X⁻ is Br⁻, A cannot be [3',4']cyclopentenyl; (c) when R¹ and R² are hydrogen and X⁻ is $ClO_4^-$, A cannot be phenyl; and (d) when R¹ is hydrogen, R² is 9-methyl and X⁻ is $ClO_4^-$, A cannot be phenyl.

The invention further relates to a method for the treatment or prevention of neurodegenerative disorders or neurotoxic injuries which comprises administering to a patient in need of such treatment an effective amount of a compound of the formula:

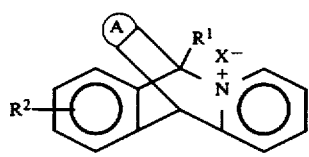

wherein:

R¹ is hydrogen, or lower-alkyl;

R² is hydrogen, or from one to four, the same or different, substituents in any of the 7-,8-,9- or 10- positions selected from the group consisting of halogen, nitro, lower-alkoxy, hydroxy, and lower-alkyl;

A is a member selected from the group consisting of cycloalkenyl, tetrahydrofuranyl, cycloalkyl, cycloalkenyl substituted at any available carbon atom thereof by lower-alkylidene; and phenyl; and X⁻ is an anion;

or a hydrate thereof; or a stereoisomer thereof; with the following provisos a) when R¹ is hydrogen, R² is 9-nitro and X⁻ is $ClO_4^-$, A cannot be [3',4']cyclopentenyl; b) when R¹ is hydrogen, R² is 7,10-dihydroxy and X⁻ is Br⁻, A cannot be [3',4']cyclopentenyl; (c) when R¹ and R² are hydrogen and X⁻ is $ClO_4^-$, A cannot be phenyl; and (d) when R¹ is hydrogen, R² is 9-methyl and X⁻ is $ClO_4^-$, A cannot be phenyl.

DETAILED DESCRIPTION INCLUSIVE OF PREFERRED EMBODIMENTS

The term lower-alkyl as used herein means linear or branched hydrocarbon chains having one to about four carbon and thus includes methyl, ethyl, isopropyl, n-butyl, sec-butyl, and the like.

The term halogen as used herein means bromine, chlorine, iodine, and fluorine.

The term lower-alkoxy as used herein means linear or branched alkyloxy substituents having one to about four carbon atoms and thus includes methoxy, ethoxy, propoxy, isopropoxy, butoxy, sec-butoxy, and the like.

The term cycloalkenyl as used herein means $C_5$ through $C_7$ unsaturated monocyclic hydrocarbon residues and thus includes cyclopentenyl, cyclohexenyl and cycloheptenyl.

The term cycloalkyl as used herein means $C_5$ through $C_7$ unsaturated monocyclic hydrocarbon residues and thus includes cyclopentyl, cyclohexyl and cycloheptyl.

The term lower-alkylidene as used herein means linear or branched hydrocarbon chains having one to about four carbon atoms and thus includes methylidene, ethylidene, propylidene, isopropylidene, sec-butylidene and the like.

The term anion (X⁻) as used herein means the anion of an organic acid (includes anions of organic monoacids, as well as monoanions of organic diacids) which is at least as strong as acetic acid, and thus includes anions of such acids as acetic acid, methanesulfonic acid, toluenesulfonic acid, trifluoromethanesulfonic acid, (−)-dibenzoyl-L-tartaric acid [(−)-DBT], (+)dibenzoyl-D-tartaric acid [(+)-DBT], and the like; or it means an inorganic acid anion such as chloride, bromide, perchlorate, $PF_6^-$ and the like, preferably chloride.

The numbering system used throughout the specification is shown in the ring system which is illustrated below. Ring systems of this type are usually named in the chemical literature as a 6,11-substituted-6,11-dihydrobenzo[b]quinolizinium

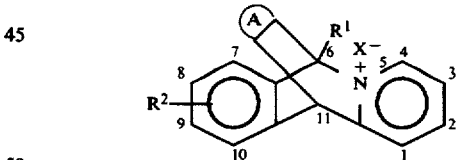

nolizinium or a 6,11-dihydro-6,11-substituted acridizinium. It should be noted, however, that in some of the earlier chemical literature references (see references cited in Information Disclosure Statement) ring systems of this type were numbered as shown below, and were named as a 9,10-substituted-9,10-dihydro-4a-azoniaanthracene, or a 9,10-dihydro-4a-azonia-9,10-substituted

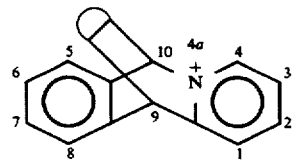

anthracene. Throughout this specification, however, we will use the former numbering system, and we will name the compounds as 6,11-substituted-6,11-dihydrobenzo[b]quinolizinium salts.

The synthesis of the compounds of the invention may be outlined as shown in Scheme A:

Scheme A

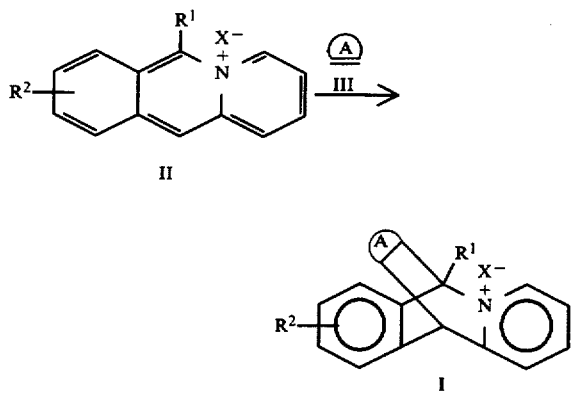

A suitably substituted benzo[b]quinolizinium salt of Formula I can be treated with an excess of an appropriate cyclic diene or olefin of the Formula III, in a suitable solvent, e.g. acetonitrile, sulfolane, nitromethane, water, or alcoholic solvents, e.g. methanol, or mixtures of said solvents, at a temperature in the range of about room temperature up to the boiling point of the solvent or solvent mixture used to produce the 6,11-substituted-6,11-dihydrobenzo[b]quinolizinium salts of Formula I where A is cycloalkenyl, tetrahydrofuranyl, cycloalkyl, or cycloalkenyl substituted at any available carbon atom thereof by lower-alkylidene. The corresponding compounds of the Formula I wherein A is a phenyl ring can be prepared by procedures which are known in the art of chemistry, for example, treating an appropriately substituted benzo[b]quinolizinium salt of Formula II in a suitable solvent, e.g. acetonitrile, concurrently with an excess of isoamyl nitrite and anthranilic acid (forms benzyne in situ) in the same solvent, followed by the addition of ether to precipitate the compounds of Formula I wherein A is phenyl (see, for example, Fields et al., J. Org. Chem. 1971, 36(20), 2995–3001).

If desired, the compounds of Formula I can be converted into other compounds of Formula I which possess various different anions (X−) by a) treating a solution of a compound of the Formula I in water with at least one molar equivalent of the alkali metal salt of an organic acid anion or an inorganic acid anion, M+X−, wherein the acid of the salt used is a stronger acid than the corresponding acid of the initial acid anion (X−), and wherein M+ is an alkali metal, e.g. lithium, sodium or potassium; b) passing a compound of the Formula I wherein X− is other than Cl− through a Dowex ® 1×2-200 ion-exchange resin (Dowex ®-1-chloride) column to produce compounds of the Formula I wherein X− is Cl−; or c) by passing a compound of the Formula I through a suitable ion-exchange resin column (prepared, for example, by treating Dowex ® 1X2-200 ion-exchange resin with a suitable organic acid or inorganic acid) to provide various compounds of Formula I wherein X− is other than Cl−, ClO4− or PF6−.

It will be appreciated that the compounds of the Formula I can possess one or more asymetric carbon atoms and are thus capable of existing in a number of stereoisomeric forms, e.g. enantiomers, diastereomers, and geometric isomers. Unless otherwise specified herein, the, invention is intended to extend to each of these stereoisomeric forms, and to mixtures thereof, including the racemates. In some cases there may be advantages, e.g. greater potency, to using a particular enantiomer when compared to the other enantiomer or the racemate in the treatment or prevention of neurodegenerative disorders or neurotoxic injuries, and such advantages can be readily determined by those skilled in the act. The different stereoisomeric forms may be separated one from the other by the methods described hereinbelow:

The diastereomers/geometric isomers can be separated by conventional procedures which are well known in the art of chemistry such as chromatography, fractional crystallization and the like. The separation of enantiomers can be accomplished by a) chiral chromatography, or b) treating a racemic mixture of a compound of Formula I with the potassium salt of (+)-dibenzoyl-D-tartaric acid (K+[(+)-DBT]) to afford a compound of Formula I as the −[(+)-DBT] salt; fractional crystallization of the −[(+)-DBT] salt to afford a single diastereomer of the −[(+)-DBT] salt, and then conversion of the single diastereomer of the −[(+)-DBT] salt into various other non-chiral anions (X−) by following the procedures described hereinabove for the conversion of compounds of the Formula I into other compounds of the Formula I with various different anions (X−), to produce the compounds of the Formula I as a single enantiomer; or c) treating a racemic mixture of a compound of Formula I with the potassium salt of (−)-dibenzoyl-L-tartaric acid (K−[(−)-DBT]) to afford a compound of Formula I as the −[(−)-DBT] salt and then proceeding as described hereinabove in part b to afford the compounds of Formula I as the other enantiomer.

The suitably substituted benzo[b]quinolizinium salts of the Formula II, which are required for the synthesis of the compounds of the Formula I, are either known and can thus be prepared by procedures which are known in the art of chemistry (see for example, Bradsher and Parham, J. Org. Chem., 1963, 28, 83–85; Bradsher and Jones, J. Am. Chem. Soc., 1957, 79, 6033–34; Bradsher et al., J. Het. Chem. 1964, 1, 30–33; and Bradsher and Parham, J. Het. Chem. 1964, 1, 121–124); or if they are novel, they can be prepared by the procedures described in the an or those,described hereinbelow and illustrated in Schemes B and C. In Scheme B, at least one molar equivalent of an appropriately substituted benzyl halide (IV), wherein Z is a halogen, preferably chlorine, bromine, or iodine, is treated with one mole of an appropriately substituted Scheme B

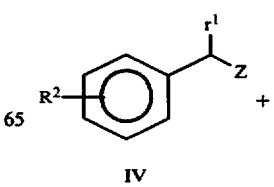

IV

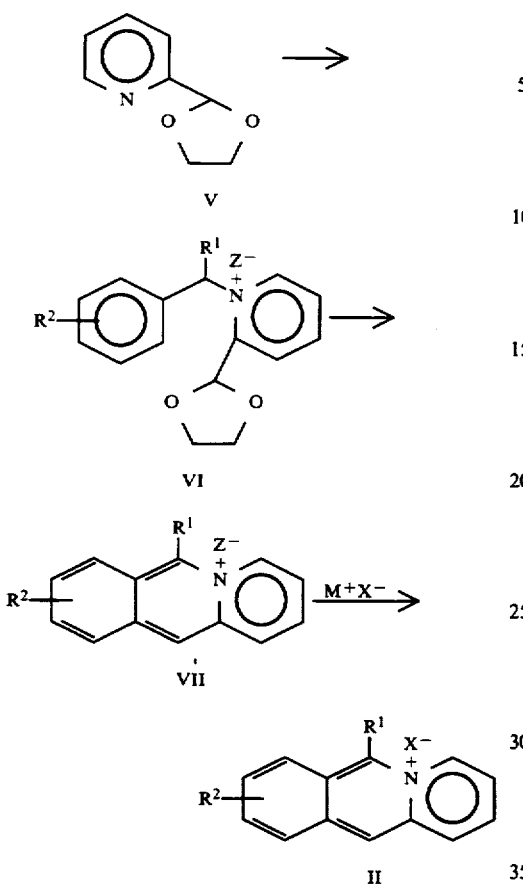

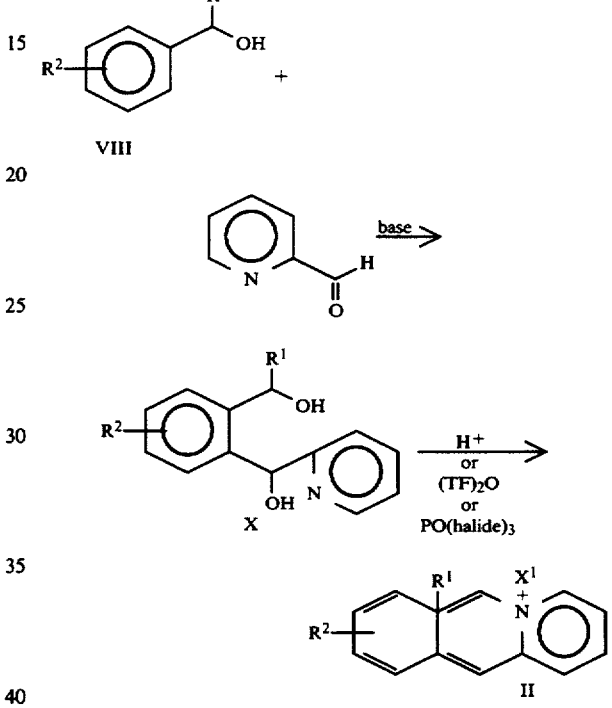

stituted 2-(1,3-dioxolan-2-yl)pyridine (V), in the presence of a solvent, e.g. sulfolane, or acetone, at a temperature in the range of about room temperature up to the boiling point of the solvent used, to produce the pyridinium salt (VI). The pyridinium salt (VI) can then be treated with an excess of an acid, e.g. polyphosphoric acid, 48% hydrobromic acid, or a mixture of polyphosphoric acid and methanesulfonic acid at a temperature in the range of about 40° C. up to the boiling point of the acid, or acid mixture used, to produce the compounds of the Formula VII (Formula II wherein $Z^- = X^- =$ halogen). The compounds of the Formula VII can then be converted into compounds of the Formula II which possess various anion groups, $X^-$, by (a) treating a compound of the Formula VII, either as a solution in water, or neat, with or adding it to an aqueous solution containing at least one molar equivalent of the alkali metal salt of an organic acid anion or an inorganic acid anion, $M^+X^-$, wherein the acid of the salt used is a stronger acid than the corresponding acid of the initial acid anion, and wherein $M^+$ is an alkali metal, preferably potassium, lithium, or sodium, and $X^-$ is as defined hereinabove; at a temperature in the range of about room temperature up to the boiling point of the aqueous solution, or (b) adding the alkali metal salt, $M^+X^-$, as a solid, to, or treating it with a solution of the compound of Formula VII in water, at a temperature in the range of about room temperature up to the boiling point of the aqueous solution.

Alternatively, the benzo[b]quinolizinium salts of Formula II can be prepared as shown in Scheme C. A suitably substituted benzyl alcohol (VIII) is treated with at least two molar equivalents of a lower-alkyl alkali metal, preferably n-BuLi, optionally in the presence of at least one mole of a second base, e.g. tetramethylethylenediamine, followed by addition of an excess of a suitable pyridine derivative (IX), in an organic solvent, such as ether; at room temperature or below, preferably at a temperature in the range of about room temperature to about $-30°$ C., to afford diol X. The diol X can then be treated with a) an excess of an acid, e.g. 45% hydrobromic acid in acetic acid, at a temperature in the range of room temperature up to the boiling point of the acid used, or b) an excess of trifluoromethanesulfonic anhydride $((TF)_2O)$, in a suitable solvent, at about room temperature or above, or c) at least one molar equivalent of a phosphorous oxyhalide, preferably phosphorous oxychloride, at about room temperature or above, to produce the compounds of the Formula II, which can in turn be converted into other benzo[b]quinolizinium salts of the Formula II which possess various different anion groups, $X^-$, by following the procedures described hereinabove. It will be noted that the method described hereinabove in Scheme C is the preferred method when it is desired to prepare compounds of the Formula II which contain substituents in the 6-, 10-, and/or 11-positions.

The appropriately substituted cyclic diene or olefin (III), the alkali metal salts of an organic acid anion or an inorganic acid anion $(M^+X^-)$, benzyl halide (IV), 2-(1,3-dioxolan-2-yl)pyridine (V), benzyl alcohol (VIII) and pyridine derivative (IX) are commercially available, or they can be prepared by procedures well known in the art, or by the procedures described hereinbelow.

The compounds of Formula I are quinolizinium salts in which it is preferred that the salts are pharmaceutically acceptable salts, that is, salts whose anions $(X^-)$ are relatively innocuous to the animal organism in pharmaceutical doses of the salts, so that the beneficial properties inherent in the compounds of the Formula I are not vitiated by side effects ascribable to the anions. In practicing the present invention it is convenient to use the anions ($X^-$) of organic acids such as methanesulfonic acid and toluenesulfonic acid, or the anions of inorganic acids such as hydrobromic acid and hydrochloric acid. However, other appropriate pharmaceutically acceptable salts within the scope of the invention are those derived from the anions ($X^-$) of other organic acids, organic diacids, or inorganic acids.

The structures of the compounds of the invention were established by the mode of synthesis, and by one or more of elemental analysis, and infrared, nuclear magnetic resonance and mass spectroscopy. The course of the reactions and the identity and homogeneity of the products were assessed by one or more of thin layer chromatography (TLC), high pressure liquid chromatography (HPLC), or gas-liquid chromatography (GLC).

The following examples will further illustrate the invention without, however, limiting it thereto. All melting points (m.p.) are in degrees centigrade (° C.) and are uncorrected.

Example 1

To a mixture of benzo[b]quinolizinium bromide (10 g, 0.04 mol) (Bradsher and Parham, J. Org. Chem. 1963, 28, 83–85, Example VIIa) in 100 mL of acetonitrile/methanol (3:1) was added 3.55 g (0.044 mol) of 1,3-cyclohexadiene in 5 mL of acetonitrile/methanol (3:1) and the resulting solution was stirred at room temperature for 3 hours. The solvent was removed in vacuo and the residue was recrystallized from ethyl acetate/methylene chloride (3×) to afford 9.3 g (67%) of 6,11[3',4']-cyclohexenyl-6,11-dihydrobenzo[b]quinolizinium bromide (Formula I: $R^1=R^2=H$; $A=[3',4']$-cyclohexenyl; $X^-=-Br^-$), as an off-white solid, m.p. 285°–290° C.

Example 2

A solution containing 11-methyl-benzo[b]quinolizinium perchlorate (1.0 g, 3.4 mmol) (Bradsher and Parham, J. Org. Chem., 1963, 28, 83–85, Example VIII) and cyclopentadiene (2 mL, 23.4 mmol) in acetonitrile (40 mL) was stirred at room temperature for 2 hours. The solvent was removed in vacuo and the residue was triturated with ethyl acetate. The solid product was filtered to afford 1.2 g (97%) of 11-methyl-6,11[3',4']cyclopentenyl-6,11-dihydrobenzo[b]quinolizinium perchlorate.

Example 3

A solution of 8-methoxybenzo[b]quinolizinium perchlorate (3.2 g, 10.3 mmol) (Bradsher and Jones, J. Am. Chem. Soc, 1957, 79, 6033–34) in acetonitrile (100 mL) and methanol (35 mL) was cooled to 0° C. under nitrogen and cyclopentadiene (3.9 g, 59 mmol) was added. The mixture was stirred at room temperature overnight, followed by refluxing the reaction mixture for an additional 4 hours. The solvent was removed in vacuo and the residue was triturated with methanol, filtered, and the yellow solid thus obtained was washed with ether to afford 1.8 g (46%) of 8-methoxy-6,11[3',4']cyclopentenyl-6,11-dihydrobenzo[b]quinolizinium perchlorate (Formula I: $R^2=8$-OCH$_3$; $R^1=H$; $A=[3',4']$-cyclopentenyl; $X^-=ClO_4^-$).

Example 4

A mixture of 2-(1,3-dioxolan-2-yl)pyridine (15.1 g, 0.1 mol) and 4-bromobenzyl-bromide (25.0 g, 0.1 mol) in tetramethylene sulfone (25 mL) was refluxed for 2 hours and allowed to stand for 16 hours. The reaction mixture was diluted with ethyl acetate (500 mL) and the solid product thus obtained was isolated by filtration to yield 37 g (92%) of 1-(4-bromobenzyl)-2-(1,3-dioxolan-2-yl)pyridinium bromide (Formula VI: $R^2=4$-Br; $R^1=H$; $Z^-=Br^-$) as a white solid.

(b)

A mixture of 1-(4-bromobenzyl)-2-(1,3-dioxolan-2-yl)pyridinium bromide (37 g, 0.092 mol) in 48% HBr (300 mL) was refluxed with stirring for 24 hours. The reaction mixture was concentrated in vacuo and cold water (200 mL) was added to the residue. A yellow solid precipitated, which was isolated by filtration to yield 7.7 g (25%) of 9-bromobenzo[b]quinolizinium bromide (Formula VII: $R^2=9$-Br; $R^1=H$; $Z^-=Br^-$).

(c)

To a mixture of 9-bromobenzo[b]quinolizinium bromide (7.7 g (0.0227 mol) in acetonitrile (75 mL) and nitromethane (75 mL) was added with stirring a solution of methanol (30 mL) and cyclopentadiene (10 mL). The mixture was stirred for 7 hours and allowed to stand for 16 hours. The solvent was removed in vacuo and the residue was triturated with acetonitrile and the solid product thus obtained was isolated by filtration. The product was recrystallized from ethanol to yield 7.2 g (78%) of 9-bromo-6,11[3',4']cyclopentenyl-6,11-dihydrobenzo[b]quinolizinium bromide (Formula I: $R^1=H$; $R^2=9$-Br; $A=[3',4']$cyclopentenyl; $X^-=Br^-$), as a white solid, m.p. 277°–9° C. (dec).

Example 5

(a)

A mixture of 4-fluorobenzylbromide (17.5 g, 0.093 mol), sulfolane (25 mL) and 2-(1,3,-dioxolan-2-yl)pyridine (14.0 g, 0.093 mol) was stirred at room temperature for 2 hours, and then allowed to stand for 72 hours. The reaction mixture was diluted with ethyl acetate (200 mL) and the precipate thus obtained was collected by filtration and washed with ether to afford 31.08 g (98%) of 1-(4-fluorobenzyl)-2-(1,3,-dioxolan-2-yl)pyridinium bromide (Formula VI: $R^2=4$-F; $R^1=H$; $Z^-=Br^-$).

(b)

1-(4-Fluorobenzyl)-2-(1,3-dioxolan-2-yl)pyridinium bromide (31 g, 0.091 mol) was added to a mixture of polyphosphoric acid (350 g) and methanesulfonic acid (100 mL) at 40° C. and the resulting mixture was heated at 105° C. for 2 hours. The mixture was poured onto ice and the solution was treated with charcoal. The mixture was added to an excess of sodium perchlorate and the solution was chilled and allowed to stand for 16 hours. A precipitate formed, which was collected by filtration to afford 15.9 g (59%) of 9-fluorobenzo[b]quinolizinium perchlorate (Formula II: $R^2=9$-F; $R^1=H$; $X^-=ClO_4^-$), as a yellow solid, m.p. 168°–173° C.

(c)

To a mixture of 9-fluorobenzo[b]quinolizinium perchlorate (15.94 g, 0.0535 mol) in 100 mL of acetonitrile was added with stirring 18 g (0.27 mol) of cyclopentadiene. The reaction mixture was stirred at room temperature for 3 hours, then allowed to stand at room temperature for 16 hours. The solvent was removed in vacuo and the residue was triturated with ether. The ether was decanted, and the solid residue was stirred with ethyl acetate. The solid was collected by filtration and recrystallized from acetonitrile/ether to yield 14.73 g (75.5%) of 9-fluoro-6,11[3',4']cyclopentenyl-6,11-dihydrobenzo[b]quinolizinium perchlorate (Formula I: $R^1$=H; $R^2$=9-F; A=[3',4']cyclopentenyl; $X^-$=$ClO_4^{31}$), as a white solid, (m.p. 204°–5° C.).

Example 6

To a suspension of 9-nitrobenzo[b]quinolizinium perchlorate (2.6 g, 8 mmol) (Bradsher et al., J. Het. Chem. 1964, 1, 30–33) in acetonitrile (20 mL) was added cyclopentadiene (2.6 g, 0.039 mol). The mixture was stirred until a homogeneous solution was obtained and the solution was filtered. The solvent was removed in vacuo and the residue thus obtained was recrystallized from acetonitrile to afford 1.3 g (42%) of 9-nitro-6,11[3',4']cyclopentenyl-6,11-dihydrobenzo[b]quinolizinium perchlorate (Formula I: $R^2$=9-$NO_2$; $R^1$=H; A=[3',4']cyclopentenyl; $X^-$=$ClO_4^-$), as a white powder, m.p. 235°–237° C. (dec.).

Example 7

A mixture of benzo[b]quinolizinium bromide (4.0 g, 15.4 mmol) (Bradsher and Parham, J. Org. Chem. 1963, 28, 83–85, Example VIIa), dihydropyran (40 mL) and tetramethylene sulfone (20 mL) was heated to reflux for 6 hours, and then stirred at room temperature overnight. The mixture was diluted with ethyl acetate (40 mL) and the precipitate thus obtained was collected by filtration to afford 3.5 g (66%) of 6,11[2',3']tetrahydropyranyl-6,11-dihydrobenzo[b]quinolizinium bromide, as a white solid.

Example 8

A mixture of benzo[b]quinolizinium bromide (2.6 g, 10 mmol) (Bradsher and Parham, J. Org. Chem. 1963, 28, 83–85, Example VIIa), and 2,3-dihydrofuran (10 mL, 132 mmol) was heated to reflux and tetramethylene sulfone (10 mL) was added. The mixture was cooled to room temperature and stirred for 2 hours. The solvent was removed in vacuo, and the residue was stirred with ethyl acetate. A solid was collected by filtration and dried to afford 0.36 g (10%) of 6,11[2',3']tetrahydrofuranyl-6,11-dihydrobenzo[b]-quinolizinium bromide (Formula I: $R^1$=$R^2$=H; A=[2',3']tetrahydrofuranyl; $X^-$=$Br^-$), as a tan solid, m.p. 195°–200° C.

Example 9

To a solution of benzo[b]quinolizinium bromide (31 g, 0.12 mol) (Bradsher and Parham, J. Org. Chem. 1963, 28, 83–85, Example VIIa), in acetonitrile/methanol (3/1, 1000 mL) at room temperature was added in one portion freshly distilled cyclopentadiene (39.6 g, 0.6 mol). The mixture was stirred for 1.5 hours, and the solvent was removed in vacuo. The solid residue was slurried with ethyl acetate and the product was collected by filtration and the residue was recrystallized from methanol/tertbutylmethyl ether to afford 26.0 g (38%) of 6,11[3',4']cyclopentenyl-6,11-dihydrobenzo[b]quinolizinium bromide (Formula I: $R^1$=$R^2$=H; A=[3',4']cyclopentenyl; $X^-$=$Br^-$).

Example 10

(a)

A mixture of 2-(1,3-dioxolan-2-yl)pyridine (19 g, 0.126 mol) and p-methoxybenzyl bromide (30 mL) in sulfolane (50 mL) was stirred at room temperature for 4.5 days. The reaction mixture was diluted with ethyl acetate and cooled while stirring. The solvent was decanted to isolate an opaque oil. The oil was triturated with ethyl acetate (3×) and a glassy solid was filtered to yield 15.72 g (40.6%) of 1-(4-methoxybenzyl-2-(1,3-dioxolan-2-yl)-pyridinium chloride (Formula VI: $R^2$=4-$OCH_3$; $R^1$=H; $Z^-$=$Cl^-$).

(b)

A mixture of 1-(4-methoxybenzyl)-2-(1,3-dioxolan-2-yl)pyridinium chloride (15 g, 0.049 mol) in 300 g of polyphosphoric acid was allowed to react at 120° C. for 3 hours. The reaction mixture was poured onto ice with stirring. The mixture was neutralized with dibasic sodium phosphate and an aqueous solution of lithium perchlorate (1.1 equiv.) was added. The precipitated solid was filtered and dried to yield 9-methoxybenzo[b]quinolizinium perchlorate (Formula II: $R^2$=$OCH_3$; $R^1$=H; $X^-$=$ClO_4^-$), as a yellow solid.

(c)

A mixture of 13 g (0.042 mol) of 9-methoxybenzo[b]quinolizinium perchlorate and 30 mL (0.497 mol) of cyclopentadiene in 300 mL of methanol was stirred at room temperature for 24 hours. Additional cyclopentadiene (10 mL) was added and the reaction mixture was stirred for an additional 24 hours. The solvent was concentrated in vacuo and the dark residue was triturated with hexane and ethyl acetate respectively. The product was collected by filtration to afford crude 9-methoxy-6,11[3',4']cyclopentenyl-6,11-dihydrobenzo[b]quinolizinium perchlorate (Formula I: $R^2$=9=$OCH_3$; $R^1$=H; A=[3',4']cyclopentenyl $X^-$=$ClO^-$).

Example 11

(a)

To a solution of 3-methoxybenzylalcohol (50.0 g, 0.36 mol) in ether (1.1 L) at −20° C. was added n-BuLi (76.0 mL, 0.756 mol) at such a rate that the internal temperature of the reaction was maintained at less than −10° C. When the addition of n-BuLi was complete, the mixture was warmed to room temperature and stirred for 2 hours. The mixture was cooled to 0° C. and tetramethylethylene diamine (42.0 g, 0.36 mol) was added. The reaction mixture was cooled to −30° C. and 2-pyridinecarboxaldehyde (58.0 g, 0.36 mol) was added over 5 minutes. The reaction was warmed to 0° C. over a 30 minute period and was then quenched with water (500 mL). The mixture was chilled for 24 hours, and the product was collected by filtration and washed with ether. The product was recrystallized from ethanol to afford 30.0 g (34%) of α-[2-(hydroxymethyl)-6-methoxyphenyl]-2-pyridinemethanol (Formula X: $R^2$=6-$OCH_3$; $R^1$=H). The mother liquor from the recrystallization step was concentrated, diluted with ether and refrigerated for 16 hours. A solid precipitated, which was collected by filtration to afford an additional 13.1 g of the desired product for a total of 43.1 g (49%).

(b)

A solution of α-[2-(hydroxymethyl)-6-methoxyphenyl]-2-pyridinemethanol (13.1 g, 0.053 mol) in 45% hydrobromic acid in acetic acid (75 mL) was refluxed for 20 hours. Additional 45% hydrobromic acid in acetic acid (25 mL) was added and refluxing was continued for another 4 hours. The reaction mixture was cooled, poured into CH$_2$Cl$_2$ (700 mL) and stirred for several minutes. A solid precipitated, which was collected by filtration to afford 9.0 g (59%) of 10-methoxybenzo[b]quinolizinium bromide (Formula II: R$^2$=10-OCH$_3$; R$^3$=R$^4$=H; X$^-$=Br$^-$). The filtrate was concentrated in vacuo to afford 4.0 g (27%) of 10-hydroxybenzo[b]quinolizinium bromide (Formula II: R$^2$=10-OH; R$^1$=H; X$^-$=Br$^-$).

(c)

10-Methoxybenzo[b]quinolizinium bromide (4.0 g, 0.014 mol) was added to 150 mL of warm 10% potassium hexafluorophosphate in water. After stirring for 5 minutes, the precipitate which formed was collected by filtration and washed with warm water, then hexane, to afford 3.0 g (61%) of 10-methoxybenzo[b]quinolizinium hexafluorophosphate (Formula II: R$^2$=10-OCH$_3$; R$^1$=H; X$^-$=PF$_6^-$).

(d)

To a solution of 10-methoxybenzo[b]quinolizinium hexafluorophosphate (3.0 g, 8.4 mmol) in methanol/acetonitrile (3/1, 250 mL) was added freshly distilled cyclopentadiene (25 mL). The mixture was stirred at room temperature for 2 hours, and then was allowed to stand for 16 hours. The solvent was removed in vacuo and the residue was triturated with ethyl acetate and filtered to afford 2.6 g (74%) of 10-methoxy-6,11[3',4']cyclopentenyl-6,11-dihydrobenzo[b]quinolizinium hexafluorophosphate (Formula I: R$^2$=10-OCH$_3$; R$^1$=H; A=[3',4']cyclopentenyl; X$^-$=PF$_6^-$).

Example 12

(a)

A mixture of 2-(1,3-dioxolan-2-yl)pyridine (3.9 g, 0.026 mol), 1-iodoethylbenzene (6.0 g, 0.026 mol) and acetone (50 mL) was stirred at room temperature under nitrogen. The acetone was removed, and sulfolane (50 mL) and additional 1-iodoethylbenzene (0.5 equivalents) was added and the mixture was stirred for 24 hours. The mixture was diluted with ethyl acetate, and the precipitate which formed was collected by filtration to afford 3.7 g (37%) of 1-(1-phenylethyl)-2-(1,3-dioxolan-2-yl)pyridinium iodide (Formula VI: R$^2$=H; R$^1$=CH$_3$; Z$^-$=I$^-$).

(b)

A mixture of 1-(1-phenylethyl)-2-(1,3-dioxolan-2-yl)pyridinium iodide (3.5 g, 9 mmol) and 48% hydrobromic acid (20 mL) was refluxed for 16 hours. The solvent was removed in vacuo to afford 1.9 g (76%) of 6-methylbenzo[b]quinolizinium bromide (Formula VII: R$^2$=H;R$^1$=CH$_3$; Z$^-$=Br$^-$).

(c)

A mixture of 6-methylbenzo[b]quinolizinium bromide (1.8 g, 7 mmol), cyclopentadiene (2.6 g, 0.039 mol) and methanol was stirred at room temperature for 48 hours. The solvent was removed in vacuo and the residue was dissolved in water, washed with ether, treated with charcoal and filtered through celite. Sodium perchlorate (857 mg, 7 mmol) was added to the filtrate and the solution was cooled. A solid precipitated, which was collected by filtration and washed with ether to afford 365 mg (15%) of 6-methyl-6,11[3',4']cyclopentenyl-6,11-dihydrobenzo[b]quinolizinium perchlorate, .½ H$_2$O (Formula I: R$^2$=H; R$^1$=CH$_3$; A=[3',4']cyclopentenyl; X$^-$ClO$_4^-$), as a tan solid, m.p. 239°–241° C. (dec.).

Example 13

A mixture of benzo[b]quinolizinium bromide (5.0 g, 0.02 mol), (Bradsher and Parham, J. Org. Chem. 1963, 28, 83–85, Example VIIa), methanol (3 mL), water (40 mL) and cyclopentene (3.3 mL, 0.04 mL) was heated to 65° C. in a sealed tube for 2 hours. Additional methanol (5.0 mL) was added and heating was continued at 65° C. for 8 hours. Additional methanol (3.0 mL) was again added and the mixture was heated at 65° C. for about 17 hours. The solvent was removed in vacuo and the residue was purified by column chromatography on silica eluting with ethyl acetate/PAW (1/1, wherein PAW is pyridine/acetic acid/water (55/20/25) to afford two fractions, each of which contains a single geometric isomer, as well as a third fraction which contains 4.0 g of a mixture of both isomers. Each of the isomers was individually treated with water (20 mL), followed by sodium perchlorate to afford 0.2 g (2.8%) of 6,11[1',2']cyclopentyl-6,11-dihydrobenzo[b]quinolizinium perchlorate.½ hydrate (Example 13(a)) (Formula I: R$^1$=R$^2$=H; A=[1',2']cyclopentyl; X$^-$=ClO$_4^-$), as one geometric isomer, and 0.88 g (12%) of 6,11[1',2']cyclopentyl-6,11-dihydrobenzo[b]quinolizinium perchlorate.½ hydrate (Example 13(b) (Formula I: R$^1$=R$^2$=H; A=[1',2']cyclopentyl; X$^-$=ClO$_4^-$), as the other geometric isomer. The first isomer was isolated as a white solid, m.p. 198°–201° C. and the second isomer was isolated as a tan solid, m.p. 217°–222° C.

Example 14

(a)

Benzo[b]quinolizium bromide (508.5 g, 1.95 mol) was dissolved in distilled water (5L) with heating on a steam bath and potassium hexafluorophosphate (367.2 g, 1.95 mol) in water (1.1 L) was poured into this solution in portions. The mixture was stirred at ambient temperature for 3 hours, then in an ice-bath for 1 hour. The precipitate which formed was collected by filtration, washed with water and dried at 60° C. in vacuo to afford 601 g (94.8%) of benzo[b]quinolizinium hexafluorophosphate (Formula II: R$^1$=R$^2$=H; X$^-$=PF$_6^-$).

(b)

A solution of 5 g (0.0163 mol) of benzo[b]quinolizinium hexafluorophosphate and 5 g (0.047 mol) of 6,6-dimethylfulvene in nitromethane (60 mL) was allowed to reflux for 1 hour and cooled. A brown solid product (700 mg) formed, which was isolated by filtration and purified by column chromatography on silica eluting with methanol/methylene chloride (1:10) and ethyl acetate. The product isolated was passed through Dowex(Cl$^-$; 1×2-200; 50 g resin, 1000 mL water). The purified product in water was treated with NaClO$_4$ and the precipitated perchlorate was filtered and dried to yield 254 mg (4%) of 6,11-[5'-isopropylidene-[3',4']cyclopentenyl]-6,11-dihydrobenzo[b]quinolizinium perchlorate (Formula I: $R^1=R^2=H$; $A=[5'$-isopropylidene-$[3',4']$cyclopentenyl]; $X^-ClO_4^-$).

Following procedures similar to those described hereinabove, or by following procedures which are known in the art, the following known compounds (Examples 15a–15d) were prepared and, unexpectedly, they were found to bind to the PCP receptor and are thus useful in the treatment or prevention of neurodegenerative disorders or neurotoxic injuries.

Example 15

(a)

6,11-$[3',4']$cyclopentenyl-6,11-dihydrobenzo[b]quinolizinium bromide (Formula I: $R^1=R^2=H$; $A=[3',4']$cyclopentenyl; $X^-=Br^-$).

(b)

7-Nitro-6,11-benzeno-6,11-dihydrobenzo[b]quinolizinium perchlorate (Formula I: $R^1=H$; $R^2=7$-$NO_2$; $A=$phenyl; $X^-ClO_4^-$).

(c)

7-Hydroxy-10-tert-butyl-6,11-benzeno-6,11-dihydrobenzo[b]quinolizinium perchlorate (Formula I: $R^1=H$; $R^2=7$-OH,10-$C(CH_3)_3$; $A=$phenyl; $X^-ClO_4^-$).

(d)

7-Methyl-6,11-benzeno-6,11-dihydrobenzo[b]quinolizinium perchlorate (Formula I: $R^1=H$; $R^2=7$-$CH_3$; $A=$phenyl; $X^-ClO_4^-$).

BIOLOGICAL TEST RESULTS

Representative examples of the compounds of the invention have been found to possess valuable pharmacological properties. In particular, they have been found to bind to the PCP receptor and are thus noncompetitive blockers (antagonists) of the effects which excitatory amino acids, such as glutamate, have upon the NMDA receptor. The compounds of the invention are thus useful in the treatment or prevention of neurodegenerative disorders such as Huntington's disease, Alzheimer's disease, amyotrophic lateral sclerosis, Down's Syndrome, senile dementia, glutaric acidaemia type I multi-infarct dementia, Parkinson's disease, vital encephalopathies (which include, but are not limited thereto, dementia associated with HIV infections) and neuronal damage associated with uncontrolled seizures, as well as in the treatment or prevention of neurotoxic injuries associated with ischemic, hypoxic; or hypoglycemic conditions. Representative examples of such ischemic, hypoxic, or hypoglycemic conditions include strokes or cerebrovascular accidents, carbon monoxide poisoning, hyperinsulinemia, cardiac arrest, drownings, suffocation, spinal or head trauma, coronary artery bypass graft, neonatal anoxic trauma, and perinatal asphyxia.

The compounds of the invention are particularly useful in the treatment or prevention of neurotoxic injuries associated with ischemic, hypoxic; or hypoglycemic conditions, and especially ischemic, hypoxic, or hypoglycemic conditions which are associated with stroke.

The pharmacological properties of representative examples of the compounds of the invention was demonstrated by conventional in vitro biological test procedures such as the following:

[$^3$H]TCP Radioreceptor Assay (internal screen)

[$^3$H]TCP binding to PCP recognition sites was performed as described by Vignon et al. Brain Research 1983, 280, 194–197. Male Sprague-Dawley rats were sacrificed by decapitation, and whole brains were homogenized in 10 volumes (wt/vol) of cold Tris-HCl buffer (50 mM, pH 7.7) using a Brinkmann Polytron (setting 6, 30 sec). The homogenate was centrifuged at $40,000\times g$ for 10 min at 4° C. The supernatant was decanted, and the homogenization and centrifugation steps were repeated twice as described above. Following this, the pellet was resuspended in Tris-HCl (5 mM, pH 7.7) at a tissue concentration of 0.5–0.75 g/ml, and one ml aliquots were frozen at $-70°$ C. until use. The binding characteristics for PCP recognition sites were not altered by the freezing of membrane suspensions.

On the day of the assay, membrane aliquots were thawed, resuspended in fresh 5 mM Tris-HCl buffer at a tissue concentration of 1 mg/ml, and stored on ice until use. Each assay tube contained 100 µl of [$^3$H]TCP at a final concentration of approximately 1 nM, 100 µl of various concentrations of the compounds of interest, 500 µl of the tissue suspension and 300 µl of buffer to a final assay volume of 1 ml and a final protein concentration of 0.5 mg/tube. Non-specific binding was defined by addition of a final concentration of 100 µM PCP to blank tubes. All tubes were incubated at room temperature for 25 min before termination of the reaction by rapid filtration over Whatman GF/B glass fiber filters that had been presoaked in a solution of 0.5% polyethylenimine for at least 1 hr prior to use. Filters were washed with three 4 ml volumes of cold Tris buffer. Following addition of scintillation cocktail, the amount of bound radioactivity was determined by liquid scintillation spectrometry using a Beckman LS 5000TA liquid scintillation counter with an efficiency for tritium of approximately 55%. Inhibition constants ($K_i$ values) were calculated using the EBDA/LIGAND program (McPherson, J. Pharmacol. Meth. 1985, 14, 213–228), purchased from Elsevier/Biosoft, Inc. Results are reported as $K_i$ values which are expressed as the mean of at least two separate determinations; or as a percent (%) inhibition of binding at 10 µM.

Representative compounds of the invention were also tested in an external [$^3$H]TCP radioreceptor assay using the following protocol:

[$^3$H]TCP Radioreceptor Assay (external screen)

A procedure similar to that described above, for the [$^3$H]TCP radioreceptor assay (internal screen) was utilized except that the whole rat forebrain membranes were incubated at 25° C. for 60 minutes rather than at room temperature for 25 minutes, before termination of the reaction. The results are reported as a percent (%) inhibition of binding at 10 µM.

Antagonism of NMDA-induced Neurotoxicity in Cultured Neurons

Preparation of Cultured Cortical Neurons

Pregnant, Swiss-Webster mice were obtained from Taconic Farms (Germantown, N.Y.) and sacrificed 16 days post conception. Fetuses were removed and placed in a sterile dish containing Hank's balanced salt solution (HBSS), pH 7.4. Brain cortices were dissected, meninges were removed, the tissue was minced and placed into a solution of HBSS containing 0.25% (w/v) trypsin at 37° C. for 15 minutes. Tissue was then triturated with a sterile pasteur pipet, diluted with minimal essential media (Gibco 330-1430), pH 7.4, supplemented with 10% horse serum, 10% fetal calf serum, 2 mM l-glutamine, 21 mM d-glucose, 2.2 g/L sodium bicarbonate, 1000 U/ml penicillin, and 1,000 μg/ml streptomycin. Cells were plated onto Falcon primaria 96 well plates at a final density of 50,000 cells/well and incubated at 37° C. in the presence of 5% (v/v) carbon dioxide. After 5 days, plating media was replaced with maintenance media containing minimal essential media (Gibco 330-1430), pH 7.4, supplemented with 10% horse serum, 10% l-glutamine, 21 mM d-glucose, 2.2 g/l sodium bicarbonate, 1,000 U/ml penicillin, 1,000 μg/ml streptomycin, and 10 μM cytosine arabinoside. On days 7 and 10, media was replaced with maintenance media as above lacking the cytosine arabinoside. Experiments were conducted on day 13.

Neuroprotection Assessment

Day 13 cultured cortical neurons were washed twice with minimal essential media, pH 7.4 and then exposed for 30 minutes to 500 μM N-methyl-D-aspartic acid (NMDA) with or without varying concentrations of test agents. Dizocilpine (MK-801) at a final concentration of 10 μM MK-801 was routinely included as a positive control. MK-801 and test agents were prepared in minimal essential media supplemented with 21 mM d-glucose and 2.2 g/L sodium bicarbonate (MEM). After 30 minutes, media was replaced with MEM alone. Exposure of neurons to test agents was limited to the NMDA treatment period. Twenty-four hours after removal of NMDA, an aliquot of media from each well was removed for assessment of cell injury by determining lactate dehydrogenase (LDH) activity by the method of Wroblewski and LaDue Proc. Soc. Exp. Biol. Med. 1955, 90, 210–213. The results are expressed as an $IC_{50}$ (in nM) value (concentration causing 50% inhibition) for the antagonism of NMDA-induced neurotoxicity.

Table 1 summarizes the results obtained from the testing of representative compounds of the invention in the [$^3$H]TCP radioreceptor assay (internal screen and external screen) as well as in the antagonism of NMDA-induced neurotoxicity in cultured neurons.

TABLE 1

| Example Number | [$^3$H]TCP (internal screen) $K_i$(nM) or Percent Inhibition @10 μM | [$^3$H]TCP (external screen) Percent Inhibition (%) @10 μM | Antagonism of NMDA-induced neurotoxicity ($IC_{50}$ in nM) |
|---|---|---|---|
| 1 | 245 | — | — |
| 4(c) | 1626 | — | — |
| 5(c) | 806 | — | — |
| 8 | 8494 | — | — |
| 12(c) | 93.4 | — | — |
| 13(a) | 1565 | — | — |
| 13(b) | 366 | — | 8400 |
| 14(b) | 367 | — | — |
| 15(a) | 464 | 92% | — |
| 15(b) | 37% | 9% | — |
| 15(c) | 10% | 24% | — |
| 15(d) | 52% | 11% | — |

The compounds of the invention can be prepared for pharmaceutical use by conventional pharmaceutical procedures that are well known in the art; that is, by formulating a pharmaceutical composition which comprises compounds of the invention or their pharmaceutically acceptable salts together with one or more physiologically acceptable carriers, adjuvants, diluents or vehicles, for oral administration in solid or liquid form, parenteral administration, topical administration or aerosol inhalation administration, and the like.

Solid compositions for oral administration include compressed tablets, pills, powders and granules. In such solid compositions, the active compound is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

Preparations according to the invention for topical administration or aerosol inhalation administration include dissolving or suspending a compound of the invention in a pharmaceutically acceptable vehicle such as water, aqueous alcohol, glycol, oil solution or oil-water emulsion, and the like.

If desired, the compounds of the invention can further be incorporated into slow release or targeted delivery systems such as polymer matrices, liposomes, and microspheres.

The percentage of active component in such compositions may be varied so that a suitable dosage is obtained. The dosage administered to a particular patient is variable depending upon the clinician's judgment using as criteria: The route of administration, the duration of treatment, the size and physical condition of the patient, the potency of the active component and the patient's response thereto. An effective dosage amount of the active component can thus readily be determined by the clinician after a consideration of all criteria and using his best judgment on the patient's behalf.

We claim:

1. A compound of the formula:

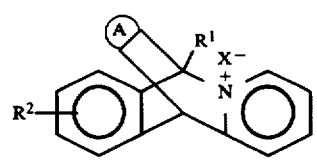

wherein:

R[1] is hydrogen, or lower-alkyl;

R[2] is hydrogen, or from one to four, the same or different, halogen substituents in any of the 7-,8-,9- or 10-positions;

A is cycloalkenyl, or said ring substituted at any available carbon atom thereof by lower-alkylidene; and X[−] is an anion;

or a hydrate thereof; or a stereoisomer thereof; with the proviso that when R[1] and R[2] are hydrogen and X[−] is Br[−], or ClO$_4$[−], A cannot be [3′,4′]cyclopentenyl.

2. A compound according to claim 1 wherein R[1] is hydrogen, or methyl; and R[2] is hydrogen or one halogen substituent in any of the 7-,8-,9- or 10-positions.

3. A compound according to claim 2 wherein R[2] is hydrogen or a bromine or fluorine substituent in any of the 7-,8-,9- or 10-positions; and A is a cyclopentenyl, or cyclohexenyl ring, or said cyclopentenyl ring substituted on any available carbon atom thereof by lower-alkylidene.

4. A compound according to claim 3 wherein R[2] is hydrogen, 9-Br or 9-F; and A is a [3′,4′]cyclohexenyl, [3′,4′]cyclopentenyl, or [5′-isopropylidene[3′,4′]cyclopentenyl] ring.

5. 6-methyl-6,11-[3′,4′]cyclopentenyl-6,11-dihydrobenzo[b]quinolizinium perchlorate according to claim 4.

6. A pharmaceutical composition which comprises a compound of the formula:

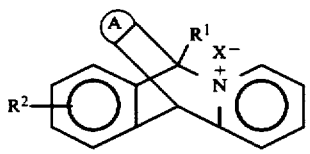

wherein:

R[1] is hydrogen, or lower-alkyl;

R[2] is hydrogen, or from one to four, the same or different, substituents in any of the 7-,8-,9- or 10-positions selected from the group consisting of halogen, nitro, lower-alkoxy, hydroxy, and lower-alkyl;

A is a member selected from the group consisting of cycloalkenyl, tetrahydrofuranyl, cycloalkyl, cycloalkenyl substituted at any available carbon atom thereof by lower-alkylidene; and phenyl; and X[−] is an anion;

or a hydrate thereof; or a stereoisomer thereof; together with a pharmaceutically acceptable carrier, adjuvant, diluent, or vehicle; with the following provisos a) when R[1] is hydrogen, R[2] is 9-nitro and X[−] is ClO$_4$[−], A cannot be [3′,4′]cyclopentenyl; b) when R[1] is hydrogen, R[2] is 7,10-dihydroxy and X[−] is Br[−], A cannot be [3′,4′]cyclopentenyl; (c) when R[1] and R[2] are hydrogen and X[−] is ClO$_4$[−], A cannot be phenyl; and (d) when R[1] is hydrogen, R[2] is 9-methyl and X[−] is ClO$_4$[−], A cannot be phenyl.

7. A pharmaceutical composition according to claim 6 wherein:

R[1] is hydrogen, or methyl;

R[2] is hydrogen, or from one to two, the same or different, substituents in any of the 7-,8-,9- or 10-positions selected from the group consisting of halogen, nitro, hydroxy, and lower-alkyl; and A is a member selected from the group consisting of cyclohexenyl, cyclopentenyl, cyclopentenyl substituted at any available carbon atom thereof by lower-alkylidene; tetrahydrofuranyl, cycloalkyl and phenyl.

8. A pharmaceutical composition according to claim 7 wherein:

R[2] is hydrogen, or from one to two, the same or different, substituents in any of the 7-,8-,9- or 10-positions selected from the group consisting of bromine, fluorine, nitro, hydroxy, methyl and tert-butyl; and A is a member selected from the group consisting of [3′,4′]cyclohexenyl, [2′,3′]tetrahydrofuranyl, [3′,4′]cyclopentenyl, cyclopentyl, [5′-isopropylidene[3′,4′]cyclopentenyl] and phenyl.

9. A pharmaceutical composition which comprises a compound according to claim 1 together with a pharmaceutically acceptable carrier, adjuvant, diluent, or vehicle.

10. A pharmaceutical composition which comprises a compound according to claim 3 together with a pharmaceutically acceptable carrier, adjuvant, diluent, or vehicle.

11. A pharmaceutical composition which comprises a compound according to claim 4 together with a pharmaceutically acceptable carrier, adjuvant, diluent, or vehicle.

12. A pharmaceutical composition which comprises a compound according to claim 5 together with a pharmaceutically acceptable carrier, adjuvant, diluent, or vehicle.

13. A method for the treatment of neurodegenerative disorders or the treatment or prevention of a neurotoxic injuries which comprises administering to a patient in need of such treatment an effective amount of a compound of the formula:

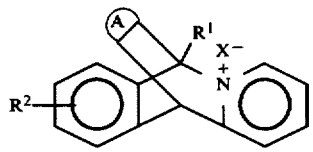

wherein:

R[1] is hydrogen, or lower-alkyl;

R[2] is hydrogen, or from one to four, the same or different, substituents in any of the 7-,8-,9- or 10-positions selected from the group consisting of halogen, nitro, lower-alkoxy, hydroxy, and lower-alkyl;

A is a member selected from the group consisting of cycloalkenyl, tetrahydrofuranyl, cycloalkyl, cycloalkenyl substituted at any available carbon atom thereof by lower-alkylidene; and phenyl; and X[−] is an anion;

or a hydrate thereof; or a stereoisomer thereof; with the following provisos a) when R[1] is hydrogen, R[2] is 9-nitro and X[−] is ClO$_4$[−], A cannot be [3′,4′]cyclopentenyl; b) when R[1] is hydrogen, R[2] is 7,10-dihydroxy and X[−] is Br[−], A cannot be [3′,4′]cyclopentenyl; (c) when R[1] and R[2] are hydrogen and X[−] is ClO$_4$[−], A cannot be phenyl; and (d) when R[1] is hydrogen, R[2] is 9-methyl and X[−] is ClO$_4$[−], A cannot be phenyl.

14. A method according to claim 13 wherein:

R[1] is hydrogen, or methyl;

$R^2$ is hydrogen, or from one to two, the same or different, substituents in any of the 7-,8-,9- or 10- positions selected from the group consisting of halogen, nitro, hydroxy, and lower-alkyl; and A is a member selected from the group consisting of cyclohexenyl, cyclopentenyl, cyclopentenyl substituted at any available carbon atom thereof by lower-alkylidene; tetrahydrofuranyl, cycloalkyl and phenyl.

15. A method according to claim 14 wherein:

$R^2$ is hydrogen, or from one to two, the same or different, substituents in any of the 7-,8-,9- or 10- positions selected from the group consisting of bromine, fluorine, nitro, hydroxy, methyl and tert-butyl; and A is a member selected from the group consisting of [3',4']cyclohexenyl, [2',3']tetrahydropyranyl, [3',4']cyclopentenyl, cyclopentyl, [5'-isopropylidene[3',4']cyclopentenyl] and phenyl.

16. A method for the treatment of neurodegenerative disorders or the treatment or prevention of neurotoxic injuries which comprises administering to a patient in need of such treatment an effective amount of a compound according to claim 1.

17. A method for the treatment of neurodegenerative disorders or the treatment or prevention of neurotoxic injuries which comprises administering to a patient in need of such treatment an effective amount of a compound according to claim 3.

18. A method for the treatment of neurodegenerative disorders or the treatment or prevention of neurotoxic injuries which comprises administering to a patient in need of such treatment an effective amount of a compound according to claim 4.

19. A method for the treatment of neurodegenerative disorders or the treatment or prevention of neurotoxic injuries which comprises administering to a patient in need of such treatment an effective amount of a compound according to claim 5.

20. A method according to claim 13 for the treatment of neurodegenerative disorders.

21. A method according to claim 13 for the treatment or prevention of neurotoxic injuries.

22. A method according to claim 21 wherein said neurotoxic injuries are associated with ischemic, hypoxic, or hypoglycemic conditions.

23. A method according to claim 22 wherein said ischemic, hypoxic, or hypoglycemic conditions are associated with stroke.

* * * * *

UNITED STATES PATENT AND TRADEMARK OFFICE
CERTIFICATE OF CORRECTION

PATENT NO.   : 5,430,036
DATED        : July 4, 1995
INVENTOR(S)  : DeHaven-Hudkins et al It is certified that error appears in the above-identified patent and that said Letters Patent is hereby corrected as shown below:

On title page,

Correct inventorship in item [75] as follows:

--Inventors: DIANE L. DEHAVEN-HUDKINS, West Pikeland Township, Chester County; WILLIAM G. EARLY, Lower Providence Township, Montgomery County; JOHN P. MALLAMO, Uwchlan Township, Chester County; MATTHEW S. MILLER, Lower Makefield Township, Bucks County, all of PA.--

Signed and Sealed this

Eighteenth Day of June, 1996

Attest:

BRUCE LEHMAN

*Attesting Officer*   Commissioner of Patents and Trademarks